(12) United States Patent
Murata et al.

(10) Patent No.: US 7,067,709 B2
(45) Date of Patent: Jun. 27, 2006

(54) FIRST AID ADHESIVE PLASTER

(76) Inventors: Takaaki Murata, c/o Aso Seiyaku Kabushiki Kaisha, Tsukure 91-1, Kikuyo-machi, Kikuchi-gun, Kumamoto-ken (JP); Masanori Yoshikawa, c/o Aso Seiyaku Kabushiki Kaisha, Tsukure 91-1, Kikuyo-machi, Kikuchi-gun, Kumamoto-ken (JP)

( * ) Notice: Subject to any disclaimer, the term of this patent is extended or adjusted under 35 U.S.C. 154(b) by 0 days.

(21) Appl. No.: 11/056,138

(22) Filed: Feb. 14, 2005

(65) Prior Publication Data

US 2005/0177086 A1    Aug. 11, 2005

(51) Int. Cl.
*A61F 5/00*    (2006.01)

(52) U.S. Cl. .......................................... 602/41; 602/54
(58) Field of Classification Search ........ 604/304–308; 602/41–43, 48, 54–59; 424/443–449
See application file for complete search history.

(56) References Cited

U.S. PATENT DOCUMENTS

| | | | | |
|---|---|---|---|---|
| 4,808,172 A | * | 2/1989 | Murata | 604/306 |
| 6,241,998 B1 | * | 6/2001 | Muchin | 424/448 |
| 6,924,410 B1 | * | 8/2005 | Tsuruda et al. | 602/48 |

FOREIGN PATENT DOCUMENTS

| | | | |
|---|---|---|---|
| GB | 2165756 A | * | 4/1986 |
| JP | 59039827 A | * | 3/1984 |
| JP | 530118 | * | 8/1993 |
| JP | 10265371 | * | 6/1998 |

* cited by examiner

*Primary Examiner*—Henry Bennett
(74) *Attorney, Agent, or Firm*—Ronald E. Greigg

(57) ABSTRACT

A first aid adhesive plaster includes an adhesive sheet, a pad member stuck onto the center of the adhesive sheet, and release papers, which are releasably stuck to the adhesive sheet and cover the pad member. The pad member comprises a pad made of a gauze, an unwoven fabric, a woven fabric or the like, and a ultraviolet blocking film disposed inside the pad or on the lower surface thereof. The pad member may be wrapped with a net.

20 Claims, 8 Drawing Sheets

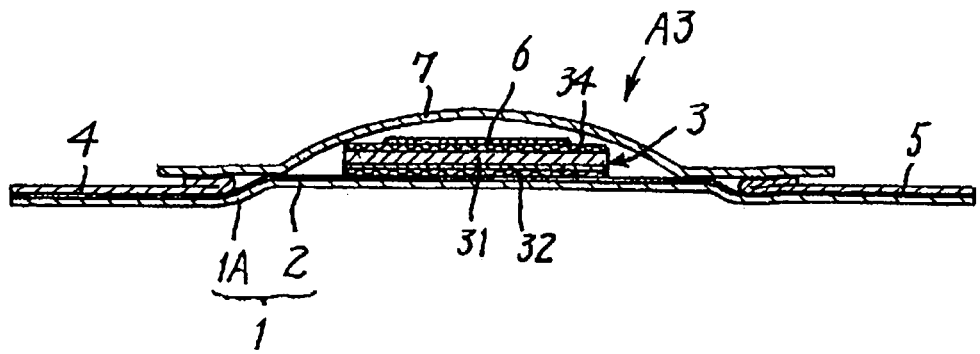
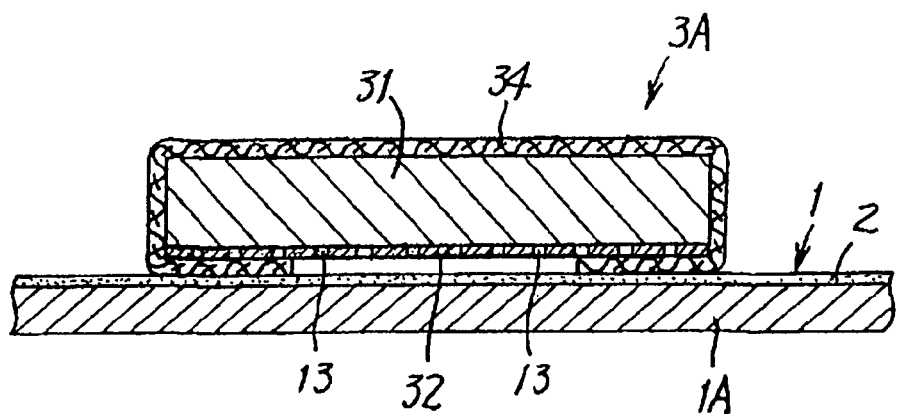
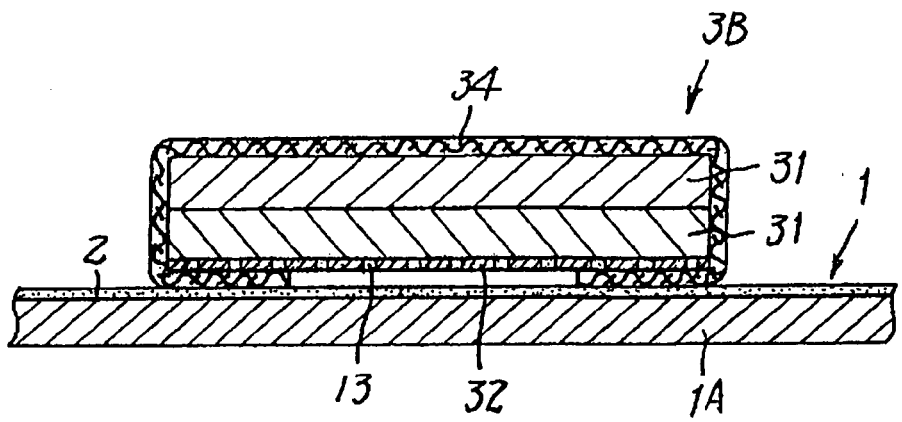

FIRST AID ADHESIVE PLASTER

BACKGROUND OF THE INVENTION

1. Field of the Invention

This invention relates to a first aid adhesive plaster for curing or disinfecting an affected part of a skin like a wound or an insect bite by sticking it on the affected part, and particularly relates to the first aid adhesive plaster which restrains delay in curing of the wound or the like or pigmentary deposit on the wounded part of the skin which are caused by exposure to ultraviolet rays and suppress an influence of the ultraviolet rays on a liquid medicament and an ointment.

2. Description of the Prior Art

A conventional first aid adhesive plaster, which is widely known, comprises an adhesive sheet having a rectangular shape, a pad of a gauze or the like stuck to a center of an upper surface of the adhesive sheet and release papers covering the upper surface of the pad and adhesive, and is separable right and left. When used, the release papers are removed and the first aid adhesive plaster is stuck to the skin in a state that the pad is placed on the affected part such as a wound. To cure or to disinfect the affected part like the wound more effectively, a first aid adhesive plaster is known in which a capsule body encapsulating a liquid medicament is placed on the pad adhering onto the adhesive sheet, as described in Japanese Utility Model No. 1,893,533, for example. When it is used, a thin film made of an aluminum foil forming a bottom face of the capsule body is broken by a projection with a sharp tip projecting downwardly from the upper part of the inner surface of the capsule body by pressing and deforming an upper part of the capsule body so that the liquid medicament in the capsule body may flow on the pad to make the pad impregnated with the medicament.

Further, as described in Japanese Patent Application No. 2001-104367, a first aid adhesive plaster is known in which an ointment is laid on the upper surface of the pad adhering onto the center of the upper surface of the rectangular adhesive sheet. The pad having a layer of the ointment is covered with a synthetic resin protecting cover, which is removably stuck to an adhesive agent layer of the adhesive sheet, and the release paper is stuck onto the adhesive layer of the adhesive sheet except the part of the protecting cover.

However, when any of the above-mentioned first aid adhesive plasters are used by sticking them to the affected part of the skin like the wound or the insect bite, exposure of the affected part to ultraviolet rays while regrowth of the skin delays regeneration of a normal skin due to penetration of the ultraviolet rays through the pad, and causes a change in a color of the skin leaving a pigmentary deposit or a trace of the wound.

In view of the circumstances, the first aid adhesive plaster has been developed as shown; for example, in Japanese Patent Application No. 5-111507 in which the adhesive sheet is formed by laying the adhesive agent layer on a supporting sheet, being a uniaxial oriented film, and the pad is stuck onto the adhesive sheet, which is covered with the release paper. The uniaxial oriented film is made of a thermoplastic resin composition prepared by compounding thermoplastic resin with inorganic filler like calcium carbonate, calcium oxide, silica, titanium oxide, or alumina, etc.; with an additive like a dispersing agent, a heat stabilizer, an ultraviolet absorber, a lubricant, or a pigment.

However, although the supporting sheet made of the thermoplastic resin and forming the adhesive sheet includes an ultraviolet blocking agent, the manufacturing cost is high since the whole supporting sheet is formed with the thermoplastic resin composition including the inorganic filler, the dispersing agent, ultraviolet blocking agent, the pigment or the like. Moreover, air permeability of the whole adhesive sheet is not enough and a rash may develop on the skin where the adhesive layer adheres. In addition, it is uneconomical to include the ultraviolet blocking agent in an unnecessary part of the plaster, being the part except the pad which is placed on the wound. Furthermore, when the necessary number of the first aid adhesive plaster are taken out of a storing bag or a storing box to be carried, the first aid adhesive plasters are exposed to the solar light (ultraviolet rays) and the efficiency of the medicine is influenced.

SUMMARY AND ADVANTAGES OF THE INVENTION

This invention is made in view of the above-mentioned problems. A purpose of the invention is to provide the first aid adhesive plaster in which an ultraviolet blocking function is demonstrated evenly and only at the area of the pad, so that it may be mass-produced at a low price and that deterioration of the efficiency of the medicine may be suppressed to the utmost even when the first aid adhesive plaster is exposed to the sun light.

In the first aid adhesive plaster to be used in a manner that the release papers stuck onto the adhesive agent layer of the adhesive sheet is removed and the adhesive sheet is stuck onto the skin in a state that the pad member stuck onto the center of he upper surface of the adhesive agent layer is placed on the affected part of the skin like the wound or the insect bite, this invention is characterized by the pad member comprising the pad to be placed on the affected part of the skin and an ultraviolet blocking film disposed on the pad.

In the meantime, the ultraviolet blocking film is the film containing fine particles like titanium oxide, zinc oxide, magnesium silicate, or magnesium oxide dispersing and reflecting ultraviolet rays, the film coated with a synthetic resin coating material compounded with such fine particles, the film containing a salicylic acid-based ultraviolet absorbing agent like salicylic acid 2-ethylhexyl, or the film coated with the synthetic resin coating material compounded with such ultraviolet absorbing agent.

In the first aid adhesive plaster structured as above, the invention relates to a preferable structure of the pad member. Namely, the preferable structure is that the ultraviolet blocking film is laid on the lower surface of the pad, or the ultraviolet blocking film is interposed between the two pads that are laminated.

Further, the invention relates to another preferable structure of the pad member. Namely, the pad member comprises the pad, a cushioning material laid on the lower surface of the pad, and the ultraviolet blocking film disposed between the pad and the cushioning material or the ultraviolet blocking film disposed on the lower surface of the cushioning material.

Furthermore, the invention relates to the first aid adhesive plaster for demonstrating an ultraviolet blocking function without using the ultraviolet blocking film. Namely, in the adhesive plaster to be used by removing the release papers stuck onto the adhesive agent layer of the adhesive sheet, and then by sticking the adhesive sheet onto the skin while placing the pad member, adhering to the center of the upper surface of the adhesive agent layer, on the affected part of the skin like the wound, at least the upper layer part or the lower layer part of the pad is formed to be an ultraviolet blocking agent layer containing an ultraviolet blocking agent.

In the first aid adhesive plaster, the invention is characterized by a net wrapping the pad member, the lower surface of which net is stuck onto the adhesive agent layer of the adhesive sheet.

The invention is characterized by the pad, constituting the pad member, which is made of the rectangular gauze or the unwoven fabric with a fixed thickness. In the invention, the ultraviolet blocking film laid on the pad of the first aid adhesive plaster described in the above claims is made of the synthetic resin film containing the ultraviolet blocking agent composed of titanium oxide, zinc oxide or a processed substance of these, or is made of the synthetic resin film coated with a layer of the ultraviolet blocking agent. The ultraviolet blocking film is formed to have a substantially the same size and shape as the form of the pad in plan view. The invention is characterized by the ultraviolet blocking film formed to be a porous film having a number of small air holes all over.

In the first aid adhesive plaster described in-the above claims the invention is characterized by the release papers stuck onto the adhesive agent layer of the adhesive sheet for covering the pad member. The invention is that the ointment is laid on the pad member, which is covered with the synthetic resin protecting cover, and the protecting cover is releasably stuck to the adhesive agent layer of the adhesive sheet. Further, the invention is that the capsule body made of synthetic resin, whose opening bottom face is closed by an aluminum foil, for encapsulating the liquid medicament is placed on the pad member. The capsule body is held on the pad member by the release papers stuck onto the adhesive agent layer of the adhesive sheet.

Further, in the first aid adhesive plaster described in the above claim, the invention is characterized by the ultraviolet blocking film which is laminated and integrated with at least the part corresponding to the encapsulated liquid medicament at least on one side face of the synthetic resin capsule body.

Furthermore, in the first aid adhesive plaster described above, the invention is characterized by the ultraviolet blocking film laminated and integrated with at least a part corresponding to the pad member on at least one side face of the protecting cover in the first aid adhesive plaster comprising the pad member, the ointment and a dome-shaped protecting cover for protecting the ointment.

According to the invention, the pad member adhering to the center of the upper surface of the adhesive layer of the adhesive sheet comprises the pad placed on the affected part of the skin like the wound and the ultraviolet blocking film disposed on the pad. Therefore, the first aid adhesive plaster having the ultraviolet blocking function is manufactured easily at a low cost only by incorporating the ultraviolet blocking film with the pad of the first aid adhesive plaster of a conventional structure in a state of layers without compounding the ultraviolet blocking agent with a base material sheet of the adhesive sheet. Further, since characteristics of the adhesive sheet like air permeability and moisture permeability are substantially effected the tendency for a rash to develop on the skin is reduced. Furthermore, delay in curing of the affected part due to the ultraviolet is eliminated and the change in the color of the skin or the pigmentary deposit is restrained by covering the affected part like the wound or the insect bite with the ultraviolet blocking film to restrain exposure of the affected part to the ultraviolet rays.

According to the invention the pad member has the structure that the ultraviolet blocking film is laid on the lower surface of the pad or is interposed between two layers of the pad, which are laminated. Therefore, the pad is provided with the ultraviolet blocking function by the ultraviolet blocking film without adversely effecting the soft touch of the pad and without damaging a lip of the wound. In addition, the pad member with the ultraviolet blocking function in a simple structure is manufactured easily.

Further, the pad member according to one embodiment of the invention comprises the pad, the cushioning material laid on the lower surface of the pad, and the ultraviolet blocking film disposed between the pad and the cushioning material or disposed on the lower surface of the cushioning material. Therefore, in addition to the effect of the pad member mentioned above the pad is softly pressed against the whole affected part like the wound by the cushioning material with a proper pressing force, and an effect of curing the affected part is promoted without damaging the wound or the like.

The invention according to one embodiment relates to the first aid adhesive plaster structured to demonstrate the ultraviolet blocking function without using the ultraviolet blocking film. Namely, the pad member has the structure that at least one of the upper layer part or the lower layer part of the pad is formed to be the ultraviolet blocking agent layer containing the ultraviolet blocking agent. Therefore, the pad member is made to have the ultraviolet blocking function while hardly affecting the air permeability and flexibility of the pad. Consequently, exposure of the affected part to the ultraviolet rays are restrained, delay in curing the affected part is eliminated, and the change in the color of the skin or the pigmentary deposit is restrained by the ultraviolet blocking layer while the pad is in soft contact with the affected part like the wound or the insect bite.

According to the invention, the pad member is wrapped with the net and the lower surface of the net is stuck onto the adhesive agent layer of the adhesive sheet. Therefore, the pad constituting the pad member and the ultraviolet blocking film are kept in a form of stably and integrally laminated layers by the net without deviation and separation even when the ultraviolet blocking film is placed on the lower surface of the pad without being stuck, and the pad member is accurately placed on the affected part like the wound. Further, when the first aid adhesive plaster is manufactured, the pad member may be handled without deforming it since the whole pad member is covered with the net, and it may be placed on an accurate position of the center of the upper surface of the adhesive sheet, resulting in improved manufacturing efficiency.

The pad constituting the pad member is made of the rectangular gauze or the unwoven fabric having a fixed thickness, as described. Therefore, the pad that excels in flexibility, air permeability and moisture permeability is provided as mentioned above. In addition, the ultraviolet blocking agent layer is easily formed by coating or impregnating at least one of the upper layer part and the lower layer part of the pad with a suspension liquid or a paste of the ultraviolet blocking agent and various additives, and then by drying it.

Further, in the first aid adhesive plaster described the ultraviolet blocking film is made of the synthetic resin film containing the ultraviolet blocking agent composed of titanium oxide, zinc oxide or a processed substance of these, or the synthetic resin film coated with a layer of the ultraviolet blocking agent. The ultraviolet blocking film having the ultraviolet blocking agent evenly on the whole surface thereof is obtained easily and at a low price by manufacturing a large ultraviolet blocking film in advance, which is then cut into a number of small ultraviolet blocking films having the same size and shape as those of a plan shape of the pad. In addition, the ultraviolet blocking film is formed to have the same size and shape as the plan shape of the pad, the whole pad has a structure to block permeation of ultraviolet rays. Therefore, an influence of the ultraviolet rays to the affected part like the wound is surely restrained. Furthermore, a curing effect on the affected part like the wound is accelerated excellently with the cooperation of the disinfectant titanium oxide or the zinc oxide.

Particularly, long wavelength ultraviolet UV-A having a wavelength of 400 to 320 nm is said to accelerate sunburn and aging of skin by depositing melanin pigments when the skin is exposed, and medium wavelength ultraviolet UV-B is said to be a cause of acute inflammation, immune suppression, skin cancer, spots and freckles when the skin is exposed. By laying the ultraviolet blocking film on the pad, which film contains or is coated with the ultraviolet blocking agent comprising an ultraviolet scattering agent or an ultraviolet absorber for blocking the UV-A and the UV-B, on the pad, or by forming the pad to have the layer of the ultraviolet blocking agent, the affected part like the wound is cured completely and effectively.

Further, according to the invention the ultraviolet blocking film has a number of small air holes all over. Therefore, air permeability of the whole pad member is secured through the small air holes formed in the ultraviolet blocking film while hardly affecting the ultraviolet blocking function and without losing air permeability of the pad placed on the affected part like the wound. In addition, in combination with the adhesive sheet having the air permeability, the adhesive sheet may be stuck to the skin including the affected part safely for a long time without causing a rash.

According to one embodiment of the first aid adhesive plaster the pad member stuck to the center of the upper surface of the adhesive sheet is covered with the release papers stuck onto the adhesive agent layer of the adhesive sheet. Therefore, when unused, the pad member may be covered and protected by the release papers for a long time. When used, the release papers are removed, the pad of the pad member is directly placed on the affected part like the wound, and the adhesive sheet is stuck to the skin, whereby the affected part is healed while effectively restraining the delay in healing of the affected part due to the ultraviolet rays by means of the ultraviolet blocking film or the ultraviolet blocking agent layer included in the pad.

According to one embodiment of the first aid adhesive plaster, the ointment is laid on the pad member stuck to the center of the upper surface of the adhesive sheet. The pad member having the layer of the ointment is covered with the synthetic resin protecting cover, which is releasably stuck to the adhesive agent layer of the adhesive sheet. Therefore, when unused, the ointment laid on the pad of the pad member is isolated from the outside air by the synthetic resin protecting cover. Consequently, the ointment is prevented from changing in its quality and from deteriorating in its effect for a long time. When used, the protecting cover is removed, the ointment laid on the pad is placed on the affected part, and the adhesive sheet is stuck to the skin, whereby the ointment promotes healing of the affected part in a short period of time. Therefore, when unused, the ointment laid on the pad of the pad member is isolated from the outside air by the synthetic resin protecting cover. Consequently, the ointment is prevented from changing in its quality and from deteriorating in its effect for a long time. When used, the protecting cover is removed, the ointment laid on the pad is placed on the affected part, and the adhesive sheet is stuck to the skin, whereby the ointment cures the affected part in a short period of time.

Further, as mentioned above, the ultraviolet blocking film disposed on the pad or the ultraviolet blocking agent layer disposed on the pad prevents the affected part of the skin like the wound from changing in color or from pigmenting, and effectively restrains a change in quality of the ointment which may be caused by the ultraviolet rays. In addition, the ultraviolet blocking film is disposed between the two pads constituting the pad member, between the pad and the cushioning material, on the lower surface of the pad, or on the lower surface of the cushioning material in a state of layers. Therefore, the ultraviolet blocking film surely prevents the ointment placed on the pad member from penetrating to reach the adhesive sheet on the lower surface side of the pad member so that the ointment may effectively work on the affected part like the wound to cure it.

Furthermore, as described by laying the ointment on a part of the net covering the upper surface of the pad member, which is wholly covered by the net, the ointment is kept at a predetermined position without coming out of the net since it is held by the mesh of the pad. In addition, when in use, the net prevents the pad from directly sticking to the affected part like the wound by the intermediary of the ointment, whereby the wound or the like is not damaged when the pad is removed after use.

According to the structure of the first aid adhesive plaster, the capsule body made of synthetic resin, whose bottom opening is closed by the aluminum foil while encapsulating a liquid medicament inside thereof, is placed on the pad member stuck to the center of the upper surface of the adhesive sheet, and the capsule body is held on the pad member by the release papers stuck to the adhesive agent layer of the adhesive sheet. Therefore, when unused, the capsule body is held on the pad member by the release papers. When used, the aluminum foil closing the bottom opening is broken by giving a pressure to the capsule body with a fingertip toward the adhesive sheet for compressive deformation, so that the liquid medicament inside may penetrate into the pad easily. After that, the release papers and the capsule body are removed, the pad is placed on the affected part like the wound, and the adhesive sheet is stuck to the skin, by which the affected part like the wound may be effectively disinfected and cured by the liquid medicament.

Further, as mentioned above, the ultraviolet blocking film arranged on the pad or the ultraviolet blocking agent layer provided on/in the pad prevents the affected part of the skin like the wound from changing in color or from pigment deposit. In addition, by arranging the ultraviolet blocking film between the two pads, between the pad and the cushioning material, on the lower surface of the pad, or on the lower surface of the cushioning material in a state of layers, the liquid medicament impregnated in the pad of the pad member is surely prevented from penetrating to reach the lower surface side of the pad member so that the liquid medicament may effectively work on the affected part to cure it.

According to the structure, the influence of the ultraviolet rays on the liquid medicament or the ointment is eliminated in advance to suppress the deterioration of the efficiency of the medicine to the utmost even when the necessary number of the first aid adhesive plasters are taken out of the storing bag or the storing box to be carried and are exposed to the sun light frequently, since the ultraviolet film is laminated with the capsule encapsulating the liquid medicament or the dome-shaped protecting cover. In this case, when the ultraviolet blocking film is laminated only with the part of the capsule contacting the liquid medicament of the part of the protecting cover contacting the ointment, the part of the lamination is limited to the minimum and the manufacturing cost is lowered.

BRIEF DESCRIPTION OF THE DRAWINGS

Other features of the invention will become apparent from the description contained herein below, taken in conjunction with the drawings, in which:

FIG. 7 is a vertically sectional side view of the first aid adhesive plaster shown in FIG. 6.

FIG. 8 is an enlarged or expanded vertically sectional side view of the pad member provided with the ultraviolet blocking film.

FIG. 9 is an expanded vertically sectional side view of the pad member provided with the ultraviolet blocking film on the lower surface of the two laminated pads.

DESCRIPTION OF THE PREFERRED EMBODIMENTS

Figure 1:
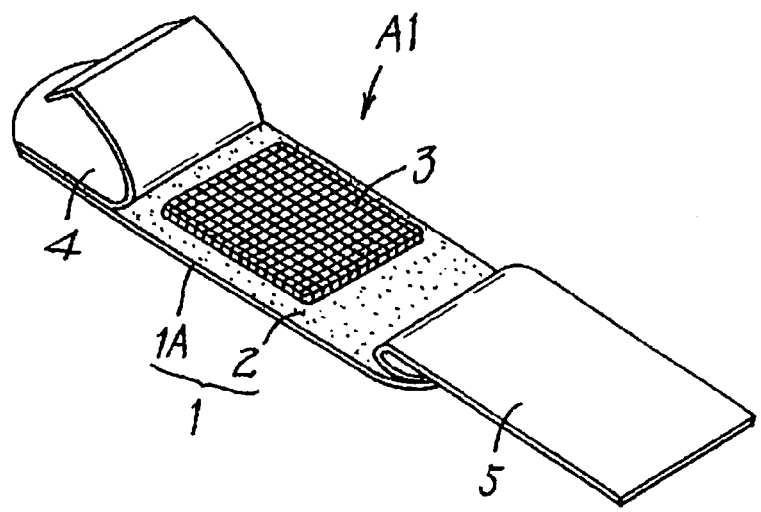
FIG. 1 is a perspective view of an embodiment of the first aid adhesive plaster of the invention wherein the release papers are turned up.
Figure 2:
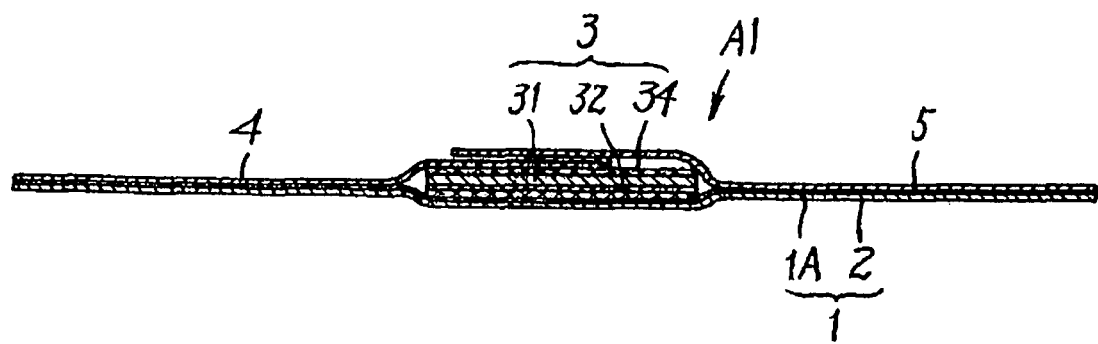
FIG. 2 is a vertically sectional side view of the first aid adhesive plaster shown in FIG. 1.

Now, a specific embodiment of the invention is described based on the drawings. A first aid adhesive plaster A1 as shown in FIGS. 1 and 2 has the structure that a pad member 3 is stuck onto the longitudinal center of an adhesive agent layer 2 of an adhesive support sheet 1 having a rectangular shape in plan view, and the pad member 3 is covered with and is held by two release papers 4, 5 releasably stuck onto the longitudinal both ends of the adhesive agent layer 2, respectively of the support sheet 1. The first aid adhesive plaster A1 is used in a manner that the release papers 4, 5 are removed from the adhesive sheet 1, and the adhesive agent layer 2 of the adhesive sheet 1 is stuck to a skin in a state that the pad member 3 is in contact with an affected part like a wound or an insect bite.

Figure 3:
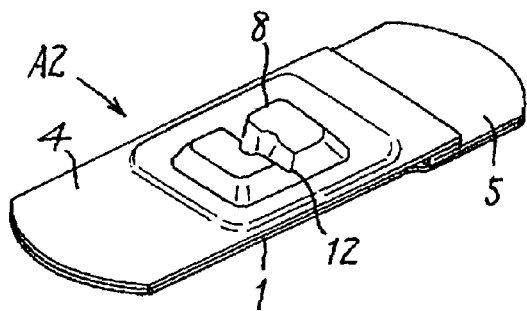
FIG. 3 is a perspective view of another embodiment of the first aid adhesive plaster.
Figure 4:
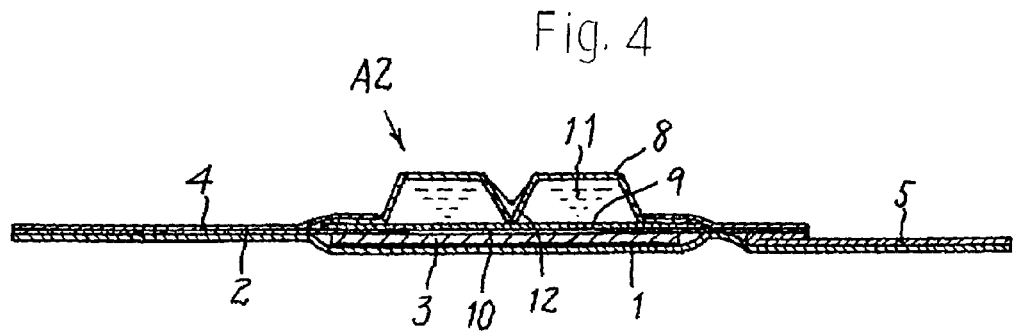
FIG. 4 is a vertically sectional side view of the first aid adhesive plaster shown in FIG. 3.
Figure 5:
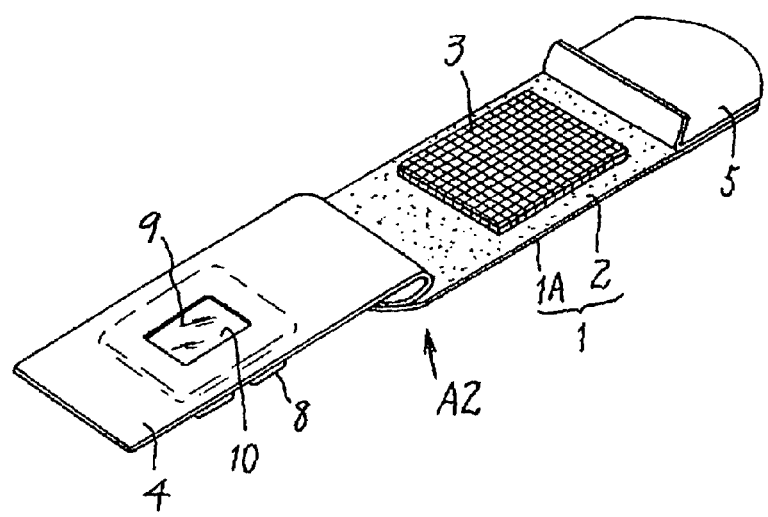
FIG. 5 is a perspective view of the first aid adhesive plaster as shown in FIG. 3, where the release papers are turned up.

In the first aid adhesive plaster A2 as shown in FIGS. 3 to 5, the pad member 3 is stuck onto the longitudinal center of the adhesive agent layer 2 of the adhesive sheet 1 having a rectangular shape in plan view, and the pad member 3 is covered with the two release papers 4, 5 releasably stuck onto the longitudinal both ends of the adhesive agent layer 2, respectively. Further, a rectangular hole 10 is formed in a part of the release paper 4 covering the pad member 3 so that a capsule body 8, which is made of a synthetic resin and encapsulates a liquid medicament 11 like a disinfectant solution, a pain relief medication or a hemostat, may be fitted to the part of the release paper having the hole 10 in a state of laminated layers. The capsule body 8 is structured in a manner that an aluminum foil 9 closes its bottom opening. The aluminum foil 9 is laid over the hole 10, and a projection 12 having a V-letter shape in cross section is formed downwardly at the center part of a top face of the capsule body 8.

When the first aid adhesive plaster A2 is used, first, the top surface of the capsule body 8 is bent by pressing it downwardly with the fingertip so that the projection 12 may stick through and break the aluminum foil 9 and that the liquid medicament 11 encapsulated in the capsule body 8 may penetrate into the pad member 3 through the hole 10. Then, the release papers 4, 5 are removed from the adhesive sheet 1. At this time, the capsule body 8 is removed together with the release paper 4. Next, the adhesive agent layer 2 of the adhesive sheet 1 is stuck to the skin in a state that the pad member 3 is in contact with the affected part like the wound or the insect bite.

Figure 6:
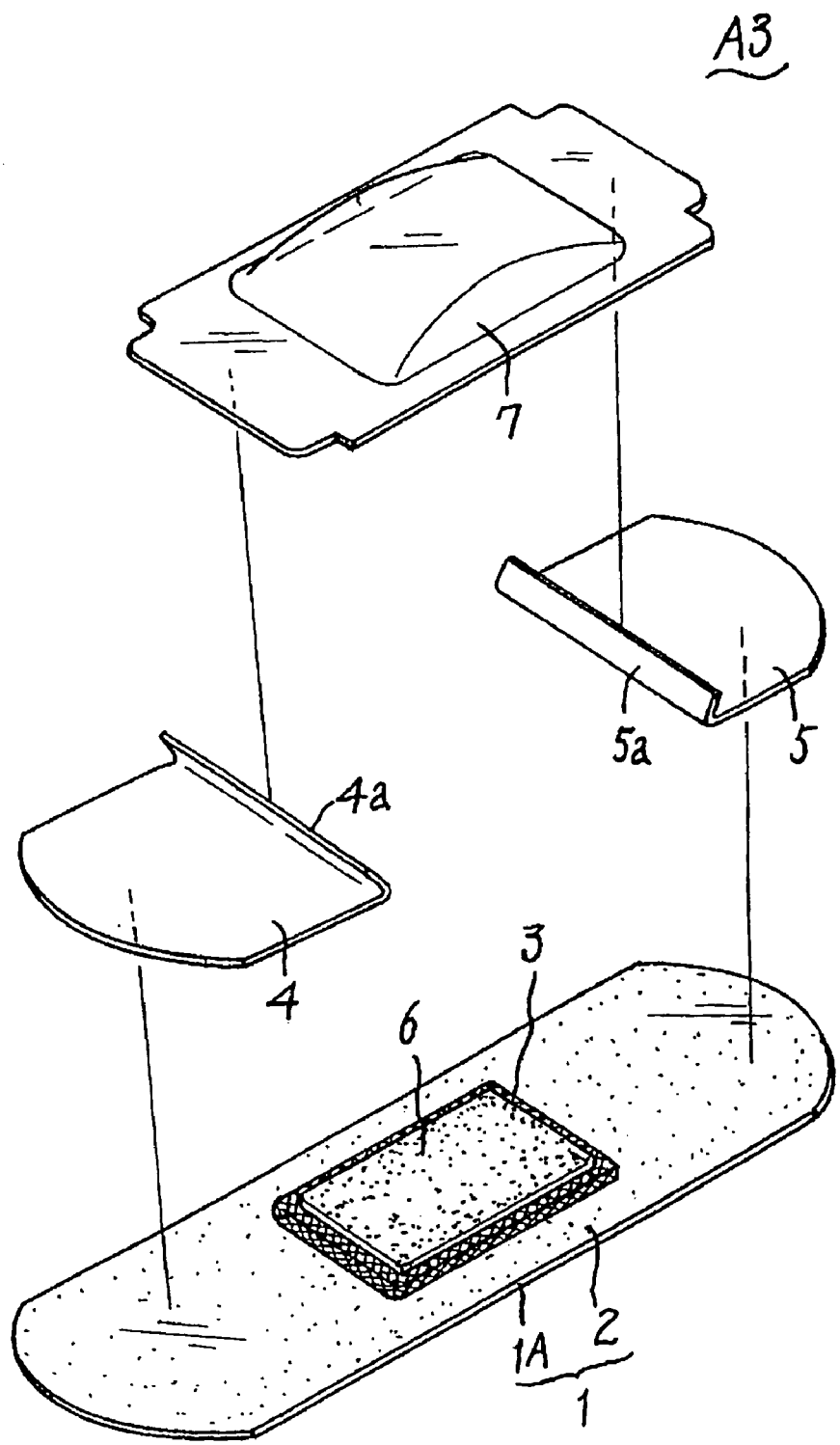
FIG. 6 is an exploded perspective view of another embodiment of the first aid adhesive plaster.

In the first aid adhesive plaster A3 as shown in FIGS. 6 and 7, the pad member 3 is stuck onto the longitudinal center of the adhesive agent layer 2 of the adhesive sheet 1 with a rectangular shape. An ointment 6 is laid on the pad member 3, and the pad member 3 having a layer of the ointment 6 thereon is covered with a protecting cover 7 made of synthetic resin like vinyl chloride resin. Both across-the-width side edges of the lower opening edge of the synthetic resin protecting cover 7 are releasably stuck to the adhesive agent layer 2 of the adhesive sheet 1, and both longitudinal ends of the adhesive agent layer 2 where the protecting cover 7 is not disposed are covered with the two release papers 4, 5 releasably stuck onto the longitudinal ends. Both of the longitudinal ends of the lower opening edges of the protecting cover 7 are laid on folded opposite ends 4a, 5a of the release papers 4, 5.

When using the first aid adhesive plaster A3, the release papers 4, 5 are removed from the adhesive sheet 1 together with the protecting cover 7 to expose the pad member 3, and the pad member 3 is brought into contact with the affected part like the wound or the insect bite. Then, the adhesive agent layer 2 of the adhesive sheet 1 is stuck to the skin in a state that the ointment 6 laid on the pad member 3 is in contact with the affected part.

Any of the three first aid adhesive plasters A1 to A3 as described above is structured to be used in a manner that the release papers 4, 5 stuck onto the adhesive agent layer 2 of the adhesive sheet 1 are removed, and then the adhesive sheet 1 is stuck to the skin in a state that the pad member 3 adhering to the center of the upper surface of the adhesive agent layer 2 is in contact with the affected part of the skin like the wound.

In these first aid adhesive plasters A1 to A3, the adhesive sheet 1 comprises a supporting sheet 1A having a rectangular shape in plan view and the adhesive agent layer 2 laid on whole of the upper surface of the supporting sheet 1A. As the supporting sheet 1A, a thin synthetic resin sheet having reasonable flexibility, elasticity, moisture permeability and light permeability, or a rectangular sheet made of unwoven fabric, woven fabric, paper or the like having a predetermined width and length is used. As the synthetic resin sheet, synthetic resins such as olefinic resin like plasticized polyvinyl chloride, amorphous polyolefin, etc.; polyester-based resin; ethylene vinyl acetate-based resin; elastomer-based resin; copolymer of olefinic resin and thermoplastic resin; polymer alloy of olefinic resin and thermoplastic elastomer; are preferable. In particular, polyolefin resin, polyester resin, or copolymer of polyolefin-based resin and thermoplastic elastomer is more preferably used.

Further, to impart the above-mentioned supporting sheet 1A properties required for a supporting body of the first aid adhesive plaster like air permeability, moisture permeability, strength, weather resistance, operability when being stuck, a non-stimulating property, etc., a sheet having a number of fine air holes all over, a sheet undergone various processes like embossing finish, uniaxial stretching, biaxial stretching, annealing or the like, or a sheet compounded with various additives or fillers, is preferably used. The additives to be used are, for example, an antioxidant, a light stabilizer, a heat stabilizer, an antistatic agent, a lubricant, a flame retardant, a color, or a dye, etc. The fillers to be used are calcium carbonate, calcium sulfate, titanium oxide, barium sulfate, magnesium hydroxide, clay or the like. These components are kneaded by various kinds of kneaders, a banbury mixer or the like, then heated, melted and kneaded to form resin pellets by using an uniaxial or biaxial extruder or the like. The pellets are then formed to be a film, which is then cut into the size of the supporting sheet 1A being the base material of the adhesive sheet 1.

The adhesive agent laid on the supporting sheet 1A to form the adhesive sheet 1 is not particularly limited as long as it is capable of releasably sticking the supporting sheet 1A to the skin, as long as it has an adhesive force capable of sticking the pad member 3 to the supporting sheet 1A, and as long as it is safe in a sense that adhesion to the skin for a long time does not cause a rash. For example, an acrylic adhesive, a rubber-based adhesive, a silicon-rubber-based adhesive, a vinyl-ether-based adhesive, or a urethane-based adhesive may be used.

Figure 10:
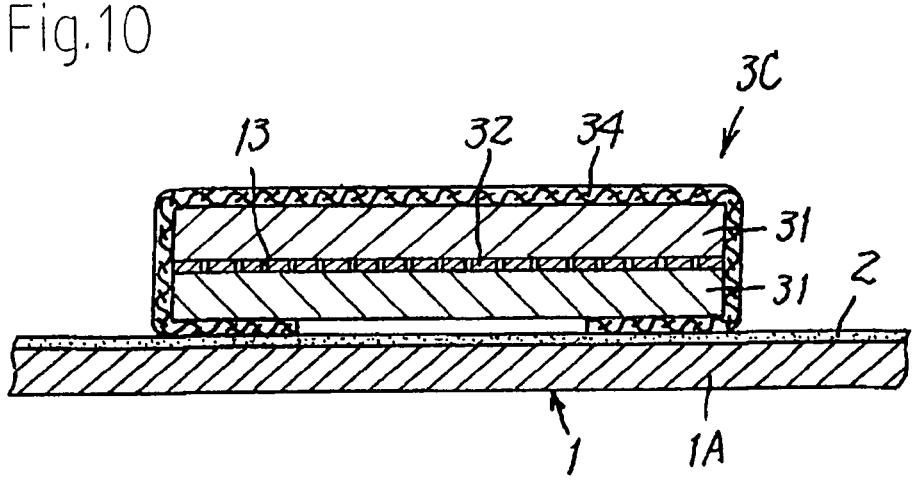
FIG. 10 is an expanded vertically sectional side view of the pad member provided with the ultraviolet blocking film between the pads.
Figure 11:
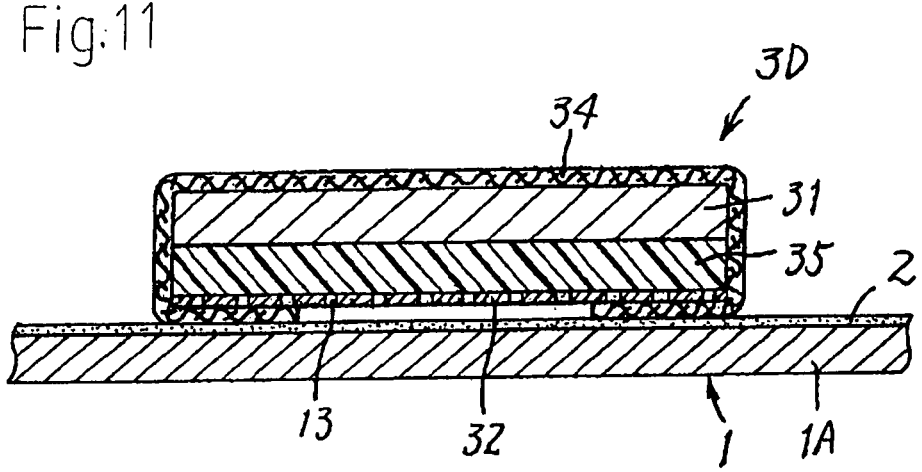
FIG. 11 is an expanded vertically sectional side view of the pad member in which the ultraviolet blocking film, cushioning material and the pad are laid.
Figure 12:
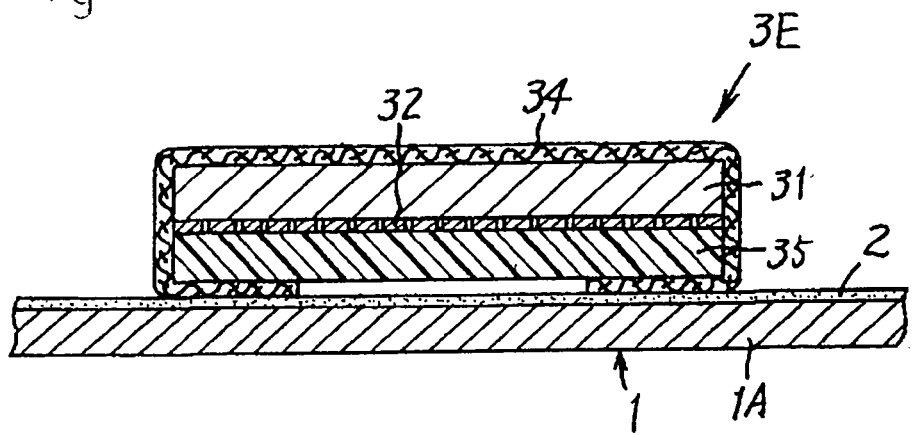
FIG. 12 is an expanded vertically sectional side view of the pad member comprising the pad, the cushioning material and the ultraviolet blocking film interposed between the pad and the cushioning material.
Figure 13:
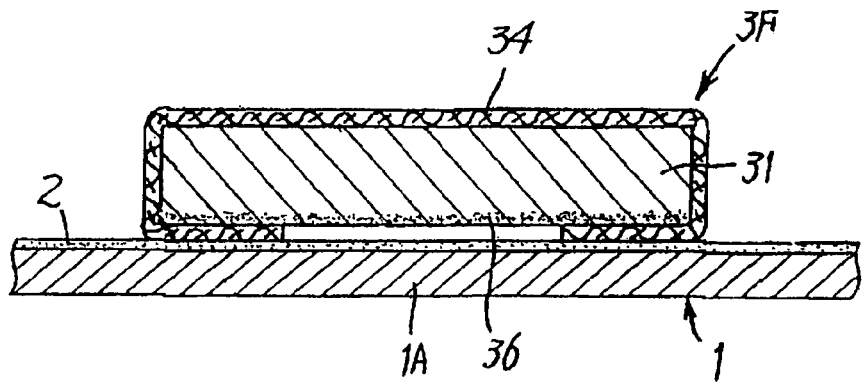
FIG. 13 is an expanded vertically sectional side view of the pad member having the ultraviolet blocking layer in the lower layer part of the pad.

The pad member 3 stuck to the center of the upper surface of the adhesive sheet 1 is the most important structural element of this invention. The pad member 3 may comprise a pad 31 and an ultraviolet blocking film 32 laid on the pad 31, as shown in FIGS. 8 to 10. It may also comprise a laminated body of the pad 31, the ultraviolet blocking film 32 and a cushioning material 35, as shown in FIGS. 11 and 12, or may also comprise the pad 31, at least one of the upper layer part or the lower layer part of which is formed to be an ultraviolet blocking agent layer 36 by impregnating the layer with an ultraviolet blocking agent as shown in FIG. 13.

The pad 31 forming an important part of the pad member 3 is the laminated body of an unwoven fabric, woven fabric or a disinfected cloth like a gauze. The pad 3 is formed to be a rectangle in plan view having a fixed thickness, a width smaller than that of the adhesive sheet 1 and a length smaller than that of the adhesive sheet 1. The ultraviolet blocking film 32 is a synthetic resin film like a polyester film containing the ultraviolet blocking agent comprising an ultraviolet dispersing agent or an ultraviolet absorbing agent or comprising both of these agents, or a synthetic resin film like a polyester film having the ultraviolet blocking layer provided by coating its surface with the ultraviolet blocking agent. The ultraviolet blocking film 32 is formed to be a rectangle having a substantially same size as the pad 31. In the meantime, a thickness of the synthetic resin film is not particularly limited, however, about 1 to 500 μm is preferable, and in particular, about 1 to 20 μm is preferably used.

The pad member 3 having the ultraviolet blocking layer 36 on the pad 31 and without having the ultraviolet blocking film 32 is prepared as follows. Namely, the upper layer part or the lower layer part of the pad 31 is coated with or impregnated with the suspension liquid or the paste of the ultraviolet blocking agent comprising the ultraviolet dispersing agent or the ultraviolet absorbing agent, and various additives. The pad 31 is then heated and dried to make the pad member 3. The pad member 3 may also be prepared in a manner that the upper layer part or the lower layer part of the pad 31 is coated with a dispersion liquid of the ultraviolet blocking agent and the additives, and it is heated and dried.

The ultraviolet blocking agent means the substance or combination of the substances that substantially blocks the ultraviolet rays in a ultraviolet range of UV-B (wavelength of 320 to 290 nm) to UV-A (wavelength of 400 to 320 nm). As such substances, both of the ultraviolet dispersing agent for blocking permeation of ultraviolet rays to the affected part or a medicament by dispersing the ultraviolet, and the ultraviolet absorbing agent for blocking permeation of ultraviolet to the affected part or to the medicament by absorbing rays of the wavelength in the ultraviolet range, may be used. To substantially block the ultraviolet rays means to block the ultraviolet rays to suppress the optical transparency of the ultraviolet range of UV-B to UV-A not to ruin the object of the invention, and a preferable ultraviolet cutting ratio is 95% or more, and more preferably it is 98% or more.

The ultraviolet dispersing agent is not particularly limited as long as it prevents the ultraviolet rays from permeating, by dispersing and reflecting or absorbing the ultraviolet rays in a physical mechanism. To be specific, for example, substances as mentioned below are preferably used. Namely, titanium oxide, zinc oxide, black iron oxide, yellow iron oxide, kaolin, talc, magnesium silicate, magnesium oxide, light (settled) magnesium carbonate, heavy magnesium carbonate, a substance made by converting these into ultra-fine particles, and in particular, titanium oxide, zinc oxide or titanium oxide covered with clay mineral, titanium oxide containing iron, and treated substances like fine particles of zinc oxide or of titanium oxide, are preferably used. These ultraviolet dispersing agents may be used in proper combination with the other ultraviolet dispersing agents or the other ultraviolet absorbing agents taking the characteristic of each of the substances into consideration. A preferable average particle diameter, at one time, of the particles of these substances applied to the ultraviolet blocking first aid adhesive plaster is about 0.001 to 30 μm, and about 0.01 to 20 μm is particularly preferable.

The ultraviolet absorbing agent is not particularly limited as long as it absorbs energy through a chemical mechanism, turns it into the energy like heat to prevent permeation of ultraviolet rays. To be specific, various kinds of ultraviolet absorbing agents may be used like a salicylic acid-based ultraviolet absorbing agent like salicylic acid 2-ethylhexyl (octyl) absorbing UV-B, a benzophenone-based ultraviolet absorbing agent like oxybenzone absorbing UV-B to UV-A of short wavelength, a cinnamic acid-based ultraviolet absorbing agent like p-methoxycinnamic acid2-ethylhexyl (oxtyl) absorbing UV-B, a benzotriazole-based ultraviolet absorbing agent like 2-(2-hydroxy-5-methylphenyl) benzo-triazol, a cyanoacrylate-based ultraviolet absorbing agent like salicylic acid 2-ethylhexyl, (2-ethylhexyl-2-cyano-3,3-diphenyl acrylate, paraminobenzoic acid, octyl p-dimethy-laminobenzoate, salicylic acid homosalate, etc.

The above-mentioned ultraviolet blocking film 32 containing such ultraviolet blocking agent in it or coated with the ultraviolet blocking agent is manufactured in a manner as mentioned below. Namely, for example, the ultraviolet blocking film containing the ultraviolet blocking agent in it is obtained in a manner that the ultraviolet blocking agent is mixed into the dispersion liquid like an aqueous dispersion liquid of polyolefin-based resin such as polyethylene-based thermoplastic resin together with various kinds of additives, which is then heated, kneaded, formed to be the film, cooled and hardened, or cross-linked.

The ultraviolet blocking film 32 coated with the ultraviolet blocking agent is obtained as follows. Namely, for example, the dispersion liquid like the aqueous dispersion liquid of polyolefin-based resin such as polyethylene-based thermoplastic resin and various additives are mixed without adding the ultraviolet blocking agent, which are heated, kneaded, formed to be film-like, cooled and hardened or cross-linked to obtain a resin film. The surface of the resin film is then coated with a liquid substance including the ultraviolet blocking agent by using a calendar roller or the like. The ultraviolet blocking film 32 is also obtained by incorporating the ultraviolet blocking agent with polyester-based urethane resin and vinyl acetate chloride copolymer resin, and dispersion liquid incorporated with the various additives is printed on the synthetic resin film by a gravure coater, which is than dried.

It is preferable that a number of small air holes 13 are formed in the ultraviolet blocking film 32 all over to impart good air permeability and moisture permeability. Preferable diameter of the small air holes 13 is about 50 to 70 μm and the preferable number of the holes 13 is about 1 to 15/cm$^2$.

Now, various structures of the pad member 3, being the most important element of the invention, are explained hereinafter. The pad member 3A shown in FIG. 8 is the laminated body of a sheet of the pad 31 made of the gauze, the unwoven fabric, the woven fabric or the like having a fixed thickness, and the ultraviolet blocking film 32. The pad 31 is laminated on the ultraviolet blocking film 32, which laminated body is wrapped with the net 34 made of the thermoplastic synthetic resin like polyethylene, and the net 34 is fixed to the lower surface of the ultraviolet blocking film 32 by means of heat welding or a proper adhesive agent. The pad member 3A is arranged on the adhesive sheet 1 in a manner that the lower surface of the net 34 covering the ultraviolet blocking film 32 is stuck onto the longitudinal center of the adhesive agent layer 2 of the adhesive sheet 1 with the ultraviolet blocking film 32 of the pad member 3A facing down. The net 34 may be netted with a string-like object made of a material other than the thermoplastic synthetic resin.

The pad member 3B shown in FIG. 9, comprises the laminated body of two pads 31, 31, which is made of the gauze, the unwoven fabric or the woven fabric and has a fixed thickness, and the ultraviolet blocking film 32. The laminated body, in which the ultraviolet blocking film 32 is laid under the lower surface of the lower pad 31 of the two laminated pads 31, 31, is wrapped with the net 34. Both ends of the net 34 are fixed to the lower surface of the ultraviolet blocking film 32 by means of heat welding or with the proper adhesive agent. The lower surface of the net 34 covering the ultraviolet blocking film 32 arranged on the lower side of the pad member 3B is stuck onto the adhesive agent layer 2 at the longitudinal center of the adhesive sheet 1.

The pad member 3C shown in FIG. 10 comprises the laminated body of the two pads 31, 31 and the ultraviolet blocking film 32 interposed between them, and the net 34 wrapping the laminated body. Both ends of the net 34 are fixed to the lower surface of the lower pad 31 by means of heat welding or a proper adhesive agent. The pad member 3C is disposed on the adhesive sheet 1 by sticking the lower surface of the net 34 covering the lower pad 31 of the pad member 3C onto the adhesive agent layer 2 at the longitudinal center of the adhesive sheet 1. In the pad members 3B and 3C shown in FIGS. 9 and 10, the number of the pads 31 is not limited to two but may be three or more.

The pad member 3D shown in FIG. 11 comprises the laminated body of the ultraviolet blocking film 32, the cushioning member 35 of synthetic risen material, for example, laid thereon and the pad 31 further laid thereon in this sequence, and the net 34 wrapping the laminated body. Both lower ends of the net 34 are fixed to the lower surface of the ultraviolet blocking film 32 disposed on the lower surface of the cushioning material 35 by means of heat welding or with the proper adhesive. The pad member 3D is disposed on the adhesive sheet 1 by sticking the lower surface of the net 34 onto the adhesive agent layer 2 at the longitudinal center of the adhesive sheet 1.

The pad member 3E shown in FIG. 12 comprises the laminated body of the pad 31, the cushioning material 35 made of foamed synthetic resin and having the same shape as the pad 31 and the fixed thickness, the ultraviolet blocking film 32 interposed between the pad 31 and the cushioning material 35, and the net 34 wrapping the laminated body. Both lower ends of the net 34 are fixed to the lower surface of the cushioning material 35 disposed on the lower side of the pad 3E by means of heat welding or the proper adhesive. The lower surface of the net 34 is stuck onto the adhesive agent layer 2 at the longitudinal center of the adhesive sheet 1.

Each of the pad members 3A, 3B and 3C comprising the laminated body formed by combining the pad 31 and the ultraviolet blocking film 32 is laminated simply by laying one on the other without sticking the pad 31 to the ultraviolet blocking film 32. Therefore, it comes apart and may not be disposed on the adhesive sheet 1 as it is. To solve the problem, the net 34 covers the laminated body of the pad 31 and the ultraviolet blocking film 32 from the upper surface of the pad 31 to extend to both sides of the laminated body, and both lower ends of the net 34 extend and are folded to the lower surface of the laminated body, which ends are fixed to the lower surface of the laminated body by means of heat welding or the proper adhesive so that a form of the laminated body may be maintained by wrapping the laminated body with the net in this manner.

When in use, the net 34 prevents the pad 31 of each of the pad members 3A, 3B, and 3C from tightly adhering to the affected part of the skin like the wound. The net 34 is placed on the affected part when in use, and after use, the net 34 is capable of being removed without damaging the wound or the like. However, when the pad 31 and the ultraviolet blocking film 32 are laminated and stuck together, the net 34 is not necessarily needed.

Similarly, in each of the pad members 3D and 3E comprising the pad 31, the ultraviolet blocking film 32 and the cushioning material 35, the pad 31, the ultraviolet blocking film 32 and the cushioning material 35 are also laid simply without being stuck together. Therefore, the pad 31 comes apart and may not be disposed on the adhesive sheet 1 as it is. To solve the problem, the net 34 covers the laminated body of the pad 31 and the ultraviolet blocking film 32 from the upper surface of the pad 31 to extend to both sides of the laminated body, and both lower ends of the net 34 extend and are folded to the lower surface of the laminated body, which ends are fixed to the lower surface of the laminated body by means of heat welding or the proper adhesive so that a form of the laminated body may be maintained by wrapping the laminated body with the net in this manner. Further, similarly to the pad members 3A, 3B and 3C, the net 34 prevents the pad 31 from being directly and firmly attached to the affected part of the skin when in use. However, when the pad 31, the cushioning material 35 and the ultraviolet blocking film 32 are laminated and stuck together, the net 34 is not necessarily needed.

Figure 14:
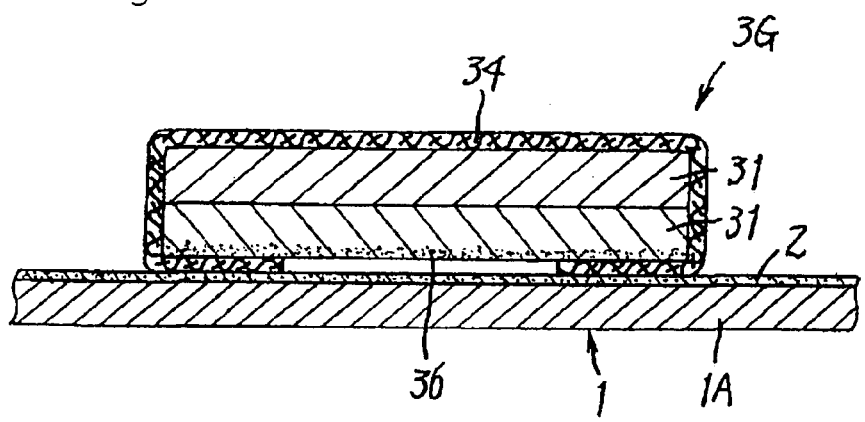
FIG. 14 is an expanded vertically sectional side view of the pad member having the ultraviolet blocking layer in the lower pad in the laminated body of the two pads.

Each of the pad members 3F and 3G shown in FIG. 13 and 14 is structured to have the ultraviolet blocking function without using the ultraviolet blocking film 32. Namely, the pad member 3F shown in FIG. 13 comprises a pad 31 and the ultraviolet blocking layer 36, which is made in a manner that the lower layer part of the pad 31 is coated with or impregnated with the ultraviolet blocking agent comprising the suspension liquid or the paste including the ultraviolet dispersing agent or the ultraviolet absorbing agent, and the various additives, which is then heated and dried. The pad member 3G shown in FIG. 14 comprises the ultraviolet blocking layer 36 provided on the lower layer part of the lower pad 31 of the two pads 31, 31. The ultraviolet blocking layer 36 is made in a manner that the lower layer part of the lower pad 31 is coated with or impregnated with the ultraviolet blocking agent comprising the suspension liquid or the paste including the ultraviolet dispersing agent or the ultraviolet absorbing agent, and the various additives, which is then heated and dried.

By wrapping the pad 31 with the net 34, these pad members 3F and 3G maintain their forms of lamination. Each of the pad members 3F and 3G, is made by fixing both lower ends of the net 34 to the lower surface of the lower pad 31 by means of heat welding or the proper adhesive. Each of them is disposed on the adhesive sheet 1 by sticking the lower surface of the net 34 onto the adhesive agent layer 2 at the longitudinal center of the adhesive sheet 1.

Each of the pad members 3A to 3G shown in FIGS. 8 to 14 is used as the pad member 3 of the first aid adhesive plaster A1 shown in FIGS. 1 and 2, or of the first aid adhesive plaster A2 shown in FIGS. 3 to 5. In the first aid adhesive plaster A1 in which the pad member 3 is directly covered with the release papers 4, 5, the release papers 4, 5 are removed from the adhesive sheet 1 when used to expose the pad member 3, and then the adhesive sheet 1 is stuck to the skin while placing the pad member 3 on the affected part like the wound. When the first aid adhesive plaster A2 in which the capsule body 8 encapsulating the liquid medicament is provided on the pad member 3 is used, first, the bottom surface made of the aluminum foil 9 of the capsule body 8 is broken by the projection 12 projecting downwardly from the top face of the capsule body 8 by pressing the top face downwardly with the finger tip to impregnate the pad 31 of the pad member 3 on the lower side with the liquid medicament in the capsule body 8. Then the release paper 4 having the capsule body 8 and the other release paper 5 are removed, and then the adhesive sheet 1 is stuck to the skin while the pad member 3 is placed on the affected part like the wound.

At this time, when the pad member 3 is any one of the pad members 3A to 3C comprising the pad 31 and the ultraviolet blocking film 32, the ultraviolet blocking film 32 is stuck to the lower side of the pad member 3, in other words, to the side of the adhesive agent layer 2 of the adhesive sheet 1, or is interposed between the two pads 31, 31. Consequently, the pad 31, which is soft, is placed on the affected part like the wound via the net 34, and the affected part like the wound is not damaged. In addition, by forming a number of small air holes 13 in the ultraviolet blocking film 32 all over substantially evenly, the rash is prevented from developing on the affected part of the skin in cooperation with the air permeability of the adhesive sheet 1 and the pad 31.

In each of the pad members 3D and 3E comprising the laminated body of the pad 31, the ultraviolet blocking film 32 and the cushioning material 35, in addition to the effect of the pad members 3A to 3C wherein the pad member 3 comprises the pad 31 and the ultraviolet blocking film 32, the pad 31 may be softly pressed against the affected skin like the wound with a moderate elasticity and without imparting a feeling of pressure because of the existence of the cushion member 35 arranged on the lower side of each of the pad members 3D, 3E.

Further, in any of the pad members 3, the ultraviolet rays penetrate through the adhesive sheet stuck to the skin, however, the ultraviolet blocking film 32 included in the pad member 3 restrains the ultraviolet rays from penetrating to the affected part like the wound, wherefore, change in the skin color or the deposit of pigment is prevented. In the meantime, in the pad members 3F, 3G shown in FIGS. 13 and 14 wherein the ultraviolet blocking layer 36, instead of the ultraviolet blocking film 32, is included in the upper or lower layer part of the pad 31, the ultraviolet blocking layer 36 prevents the ultraviolet rays, which penetrates through the adhesive sheet 1, from penetrating to the affected part.

Figure 15:
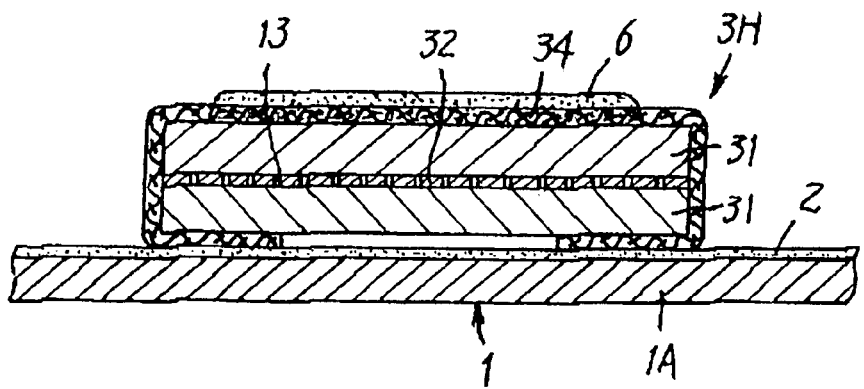
FIG. 15 is an expanded vertically sectional side view of the pad member having the layer of the ointment.
Figure 16:
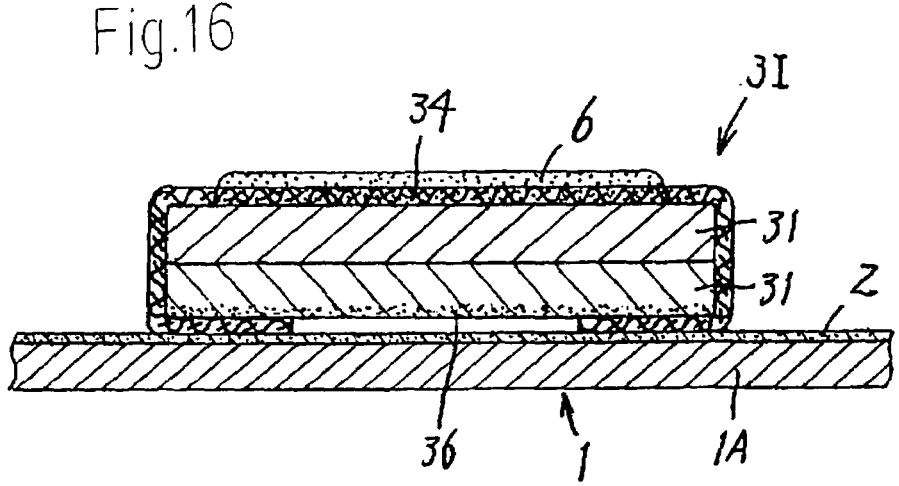
FIG. 16 is an expanded vertically sectional side view of the pad member with another structure having the layer of the ointment.

When the pad members 3A to 3G shown in FIG. 8 to 14 are used as the pad member 3 in the first aid adhesive plaster A3 shown in FIGS. 6, 7, the ointment 6 is placed on the uppermost pad 31 of the pad member 3 stuck to the adhesive agent layer 2 of the adhesive sheet 1. For example, the pad member 3H shown in FIG. 15 is formed in a manner that the layer of the ointment 6 is placed on the uppermost pad 31 of the pad member 3C, shown in FIG. 10, which is formed by wrapping the laminated body, comprising two pads 31, 31 and the ultraviolet blocking film 32 interposed between them, with the net 34. The pad member 31 shown in FIG. 16 is formed by placing the ointment 6 on the uppermost pad 31 of the pad member 3G shown in FIG. 14 comprising two pads 31, 31 and the ultraviolet blocking member 36 provided on the lower layer part of the lower pad 31.

In this manner, the pad member 3 having the layer of the ointment 6 on its surface is covered with the synthetic resin protecting cover 7, and both side edges of the lower opening edge of the protecting cover 7 are stuck onto the adhesive agent layer 2 of the adhesive sheet 1 at both long sides thereof. Both or the longitudinal lower edges of the protecting cover 7 are laid on opposite ends 4a, 5a of the release papers 4, 5 stuck to both of the longitudinal end parts of the adhesive agent layer 2 where the protecting cover 7 is not disposed.

The ointment 6 is laid on the pad 31 of the pad member 3 through the mesh of the net 34 covering the pad 31. Therefore, the ointment 6 is held by the mesh of the net 34 so that it may not flow out of the pad. In addition, even when the components of the ointment 6 penetrate into the pad 31 by capillarity, the ultraviolet blocking film 32 prevents the components from penetrating to the side of the adhesive sheet 1 in the pad member 3H shown in FIG. 15. In the pad member 31 wherein the ultraviolet blocking layer 36 is included in the pad 31 instead of the ultraviolet blocking film 32, a surface boundary between the upper and lower pads 31, 31 restrains the components of the ointment 6 from penetrating to the lower pad 31.

When the first aid adhesive plaster A3 is used, the release papers 4, 5 and the protecting cover 7 is removed from the adhesive sheet 1 to expose the pad member 3, and the adhesive sheet 1 is stuck to the skin in a state that the ointment 6 laid on the pad is put on the affected part like the wound. The effects of the ultraviolet blocking film 32 and the ultraviolet blocking layer 36, and the function of the net 34 in this state of use are already described above.

Figure 17:
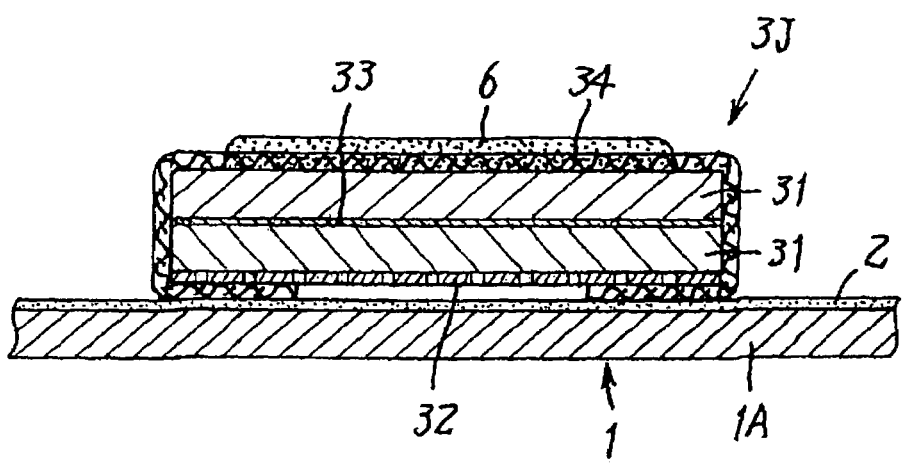
FIG. 17 is an expanded vertically sectional side view of the pad member provided with the ultraviolet blocking film and the ointment penetration restraining film.

The pad member 3J shown in FIG. 17 comprises two pads 31, 31, an ointment penetration restraining film 33 having the laminated body comprising a piece of paper or a flexible synthetic resin sheet having the same shape in plan view as the pad 31 and being interposed between the pads 31, 31, and the ultraviolet blocking film 32 layered on the lower surface of the pad 31 of the lower layer side, and the net 34 wrapping the laminated body. The ointment penetration restraining film 33 prevents the ointment from penetrating to the lower layer side. Since the other part of the structure is the same as the above-mentioned pad member 3, detailed explanation is omitted.

Figure 18:
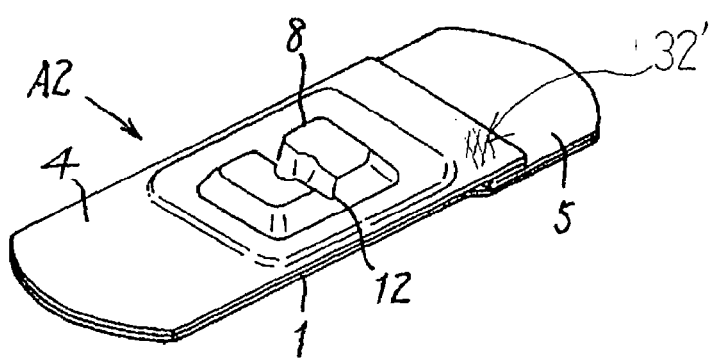
FIG. 18 is a perspective view of another embodiment of the first aid adhesive plaster.
Figure 19:
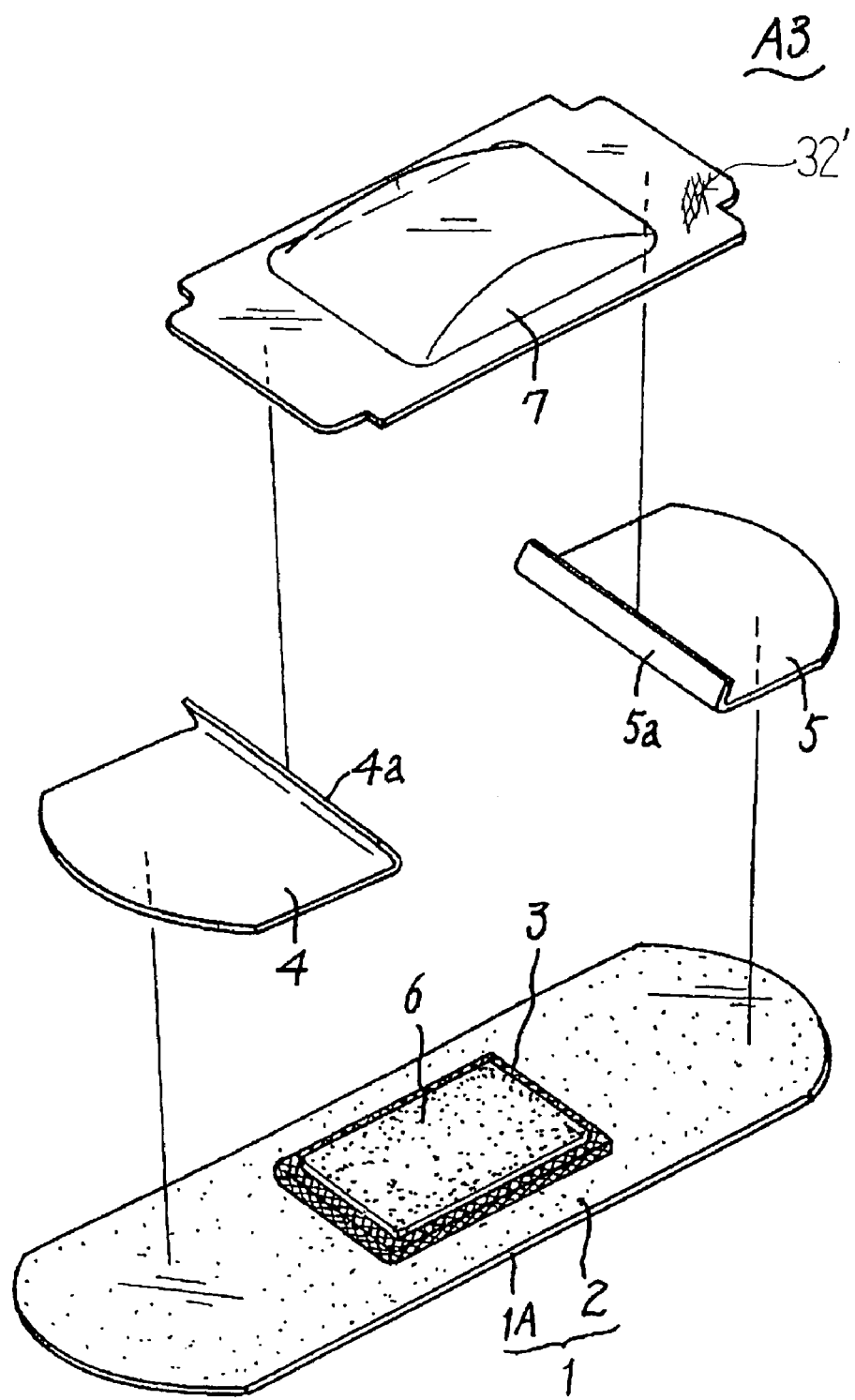
FIG. 19 is an exploded perspective view of another embodiment of the first aid adhesive plaster.

Next, another embodiment of the invention is explained in detail based on FIGS. 18 and 19. Here, the first aid adhesive plaster is covered by the ultraviolet blocking film. Namely, the main purpose is that the ultraviolet blocking film 32 prevents hindrance in regeneration of the skin caused by application of ultraviolet rays to the affected part after the first aid adhesive plaster is stuck thereto. In the meantime, the first aid adhesive plaster is not necessarily stored in a box or a case, but in many cases, the necessary number of the first aid adhesive plasters are taken out of the case, carried and then are used.

In these cases, the first aid adhesive plaster is carried in a state that the capsule body 8 as shown in FIGS. 3, 4 is exposed or that the dome-shaped synthetic resin protecting cover 7 as shown in FIG. 6 is exposed. In such case, the ultraviolet rays penetrates through the capsule body 8 or the synthetic resin protecting cover 7 and the liquid medicament 11 inside the capsule body 8 as shown in FIG. 3 or the ointment 6 as shown in FIG. 6 may be changed in the quality. It is preferable to eliminate such events in advance.

Here, as shown in FIG. 18, an ultraviolet blocking film is applied to the synthetic resin capsule body 8 shown in FIGS. 3 and 4. In this embodiment, the same ultraviolet blocking film 32' as the above mentioned one is laminated with the sheet for making the capsule body 8 before the capsule body 8 encapsulating the liquid medicament 11 is formed. The capsule body 8 is laminated and coated integrally with the ultraviolet blocking film 32' having a thickness of about 25 μ to 100 μ. The ultraviolet blocking film 32' is the synthetic resin film like polyester as described above in detail.

Further, as shown in FIG. 19, the synthetic resin protecting cover 7 as shown in FIG. 6 is coated integrally with the ultraviolet blocking film 32'. The ultraviolet blocking film 32' is the same synthetic resin film like the polyester as the one described above in detail. The ultraviolet blocking film 32' is laminated with and stuck to the inside of the sheet (to be inside of a dome) before it is formed to be a dome. The synthetic resin protecting cover 7, formed with vinyl chloride resin or the like having close compatibility and is capable of being welded, is heat-welded. However, it may be stuck by using an adhesive agent. The ultraviolet blocking film 32' may be laminated on the outside of the front/rear side of the synthetic resin protecting cover or on both sides thereof.

As mentioned above, even when the first aid adhesive plaster is taken out of the storing case or the box to be carried and is exposed to the sun light, the ultraviolet blocking film 32' eliminates the influence of the ultraviolet rays on the liquid medicament 11 inside the capsule body 8 or on the ointment 6 inside the synthetic resin protecting cover 7.

This invention may be applied to various forms of first aid adhesive plasters like a liquid medicament type using the capsule, an ointment type using a dome-shaped cover. Therefore, the first aid adhesive plaster is versatile as a plaster in an emergency medical care.

The foregoing relates to a preferred exemplary embodiment of the invention, it being understood that other variants and embodiments thereof are possible within the spirit and scope of the invention, the latter being defined by the appended claims.

What is claimed is:

1. A first aid adhesive plaster to be placed over a wound or the like and adhered to the skin, the plaster comprising,
   a flexible support sheet having an adhesive coating covering one side thereof,
   a wound-engaging pad member adhesively attached to a portion of the support sheet centrally thereof by the adhesive coating,
   an ultraviolet blocking film disposed over, laminated onto, or incorporated in the pad, and
   cover means extending over and covering the adhesive coating and the pad member, the cover means being removable to expose the adhesive coating and the pad member to permit the adhesive plaster to be adhered to the skin.

2. The first aid adhesive plaster as claimed in claim 1, wherein the ultraviolet blocking film is layered on the surface of the pad opposite the adhesive layer.

3. The first aid adhesive plaster as claimed in claim 1, wherein the pad is a laminated structure consisting of at least two layers, and wherein the ultraviolet blocking film is disposed between two adjacent layers of the pad.

4. The first aid adhesive plaster as claimed claim 1, wherein the pad member comprises a wound-engaging laminate and a second laminate of cushioning material layered between the adhesive coating and the wound-engaging laminate, and wherein the ultraviolet blocking film is disposed between the wound-engaging laminate and the cushioning material or is disposed on the surface of the cushioning material opposite the wound-engaging laminate.

5. The first aid adhesive plaster as described in claim 2, wherein the pad member is wrapped with a net, and wherein a surface of the net is adhered to the adhesive coating of the support sheet.

6. The first aid adhesive plaster as described in claim 3, wherein the pad member is wrapped with a net, and wherein a surface of the net is adhered to the adhesive coating of the support sheet.

7. The first aid adhesive plaster as described in claim 2, wherein the wound-engaging laminate of the pad member is made of a rectangular gauze or an unwoven fabric having a substantially uniform thickness.

8. The first aid adhesive plaster as described in claim 7, wherein the ultraviolet blocking film is made of a synthetic resin film coated with or containing an ultraviolet blocking agent composed of titanium oxide, zinc oxide or a processed substance of these, and wherein the ultraviolet blocking film is formed to have substantially the same size and shape as the size and shape of the pad in plan view.

9. The first aid adhesive plaster as described in claim 8, further comprising a plurality of small air holes formed in the ultraviolet blocking film dispersed over substantially its entire surface.

10. The first aid adhesive plaster as described of claim 1, further comprising an ointment layered on the wound-engaging pad member, and a synthetic resin protective cover covering the layer of ointment, the protective cover being releasably adhered to the adhesive coating of the support sheet.

11. The first aid adhesive plaster as described in claim 10, further comprising a synthetic resin capsule body having an open bottom closed with an aluminum foil and encapsulating a liquid medicament, the capsule body being placed on the pad member and held in position by the cover means adhered to the adhesive coating of the support sheet.

12. The first aid adhesive plaster described in claim 10, wherein the ultraviolet blocking film is laminated onto or integrated with at least a part of the synthetic resin capsule body.

13. In a first aid adhesive plaster to be placed over a wound or the like and adhered to the skin, the plaster including a flexible support sheet having an adhesive coating covering one side thereof, a wound-engaging pad member adhesively attached to a portion of the support sheet centrally thereof by the adhesive coating, and removable cover means extending over and covering the adhesive layer and pad member, the improvement wherein the pad member comprises an upper layer portion or a lower layer portion formed as an ultraviolet layer containing an ultraviolet blocking agent.

14. The first aid adhesive plaster as described in claim 13, wherein the pad member comprises a net wrapping and wherein a lower surface of the net wrapping is adhered onto the adhesive layer of the support sheet.

15. The first aid adhesive plaster as described in claim 14, wherein the pad of the pad member is made of a rectangular gauze or an unwoven fabric having a substantially uniform thickness.

16. The first aid adhesive plaster as described in claim 15, wherein the cover means comprises release papers adhered to the adhesive layer of the support sheet and covering the pad member.

17. The first aid adhesive plaster as described in claim 15, further comprising an ointment layered on the pad member, and a synthetic resin protective cover extending over and covering the pad member having the layer of the ointment, the protective cover being releasably adhered onto the adhesive coating of the support sheet.

18. The first aid adhesive plaster as described in claim 16, wherein the cover means comprises a synthetic resin capsule body having an open bottom closed by an aluminum foil defining a closed volume encapsulating a liquid medicament, the capsule body being disposed on the pad member and held thereon by the release papers adhered to the adhesive coating of the support sheet.

19. The first aid adhesive plaster described in claim 18, wherein the ultraviolet blocking film is laminated onto and integrated with at least the part of the capsule containing the encapsulated liquid medicament, at least on one side face of the synthetic resin capsule body.

20. The first aid adhesive plaster described in claim 17, wherein the ultraviolet blocking film is laminated onto and integrated with at least the portion of the protective cover corresponding to the pad member on at least one side face of the protective cover to protect the ointment.

* * * * *

UNITED STATES PATENT AND TRADEMARK OFFICE
CERTIFICATE OF CORRECTION

| | | |
|---|---|---|
| PATENT NO. | : 7,067,709 B2 | Page 1 of 1 |
| APPLICATION NO. | : 11/056138 | |
| DATED | : June 27, 20006 | |
| INVENTOR(S) | : Takaaki Murata et al. | |

It is certified that error appears in the above-identified patent and that said Letters Patent is hereby corrected as shown below:

Title page,

Item (30) should read as follows:

(30)    FOREIGN APPLICATION PRIORITY DATA

November 30, 2004    (JP) ………………………... 2004-346074

Signed and Sealed this

Fifth Day of September, 2006

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,067,709 B2 | Page 1 of 1 |
| APPLICATION NO. | : 11/056138 | |
| DATED | : June 27, 2006 | |
| INVENTOR(S) | : Takaaki Murata et al. | |

It is certified that error appears in the above-identified patent and that said Letters Patent is hereby corrected as shown below:

Title page,

Item (30) should read as follows:

(30) FOREIGN APPLICATION PRIORITY DATA

November 30, 2004    (JP) ………………….... 2004-346074

This certificate supersedes Certificate of Correction issued September 5, 2006.

Signed and Sealed this

Twenty-first Day of November, 2006

JON W. DUDAS
*Director of the United States Patent and Trademark Office*